United States Patent
Dong et al.

(10) Patent No.: US 8,595,164 B2
(45) Date of Patent: Nov. 26, 2013

(54) WAVELET MODELING PARADIGMS FOR CARDIOVASCULAR PHYSIOLOGICAL SIGNAL INTERPRETATION

(76) Inventors: Ming-Chui Dong, Macau (CN); Bin Bin Fu, Macau (CN); Wai Kei Lei, Macau (CN); Bing Nan Li, Tokyo (JP)

( * ) Notice: Subject to any disclaimer, the term of this patent is extended or adjusted under 35 U.S.C. 154(b) by 308 days.

(21) Appl. No.: 13/014,791

(22) Filed: Jan. 27, 2011

(65) Prior Publication Data
US 2012/0197831 A1  Aug. 2, 2012

(51) Int. Cl.
*G06E 3/00* (2006.01)
*G06E 1/00* (2006.01)

(52) U.S. Cl.
USPC .......................................................... 706/20

(58) Field of Classification Search
USPC .......................................................... 706/20
See application file for complete search history.

(56) References Cited

U.S. PATENT DOCUMENTS

| | | | |
|---|---|---|---|
| 6,002,952 A | 12/1999 | Diab et al. | |
| 6,067,462 A | 5/2000 | Diab et al. | |
| 6,549,804 B1 | 4/2003 | Osorio et al. | |
| 6,699,194 B1 | 3/2004 | Diab et al. | |
| 7,123,954 B2 | 10/2006 | Narayan et al. | |
| 7,170,404 B2 | 1/2007 | Albert et al. | |
| 7,215,986 B2 | 5/2007 | Diab et al. | |
| 7,471,971 B2 | 12/2008 | Diab et al. | |
| 7,485,095 B2 | 2/2009 | Shusterman | |
| 7,617,163 B2 * | 11/2009 | Ben-Hur et al. | 706/12 |
| 7,747,551 B2 * | 6/2010 | Snyder | 706/20 |
| 7,751,873 B2 | 7/2010 | de Voir | |
| 2004/0199482 A1 * | 10/2004 | Wilson | 706/25 |
| 2011/0047105 A1 * | 2/2011 | Sternickel et al. | 706/12 |

OTHER PUBLICATIONS

Comparison of FCM, PCA and WT techniques for classification ECG arrhythmias using artificial neural network, by Ceylan et al., published Aug. 2007.*
Comparison of extrasystolic ECG signal classifiers using discrete wavelet transforms, by Froese, published Apr. 2006.*
Wavelet transforms and the ECG: a review, by Addison, published Aug. 2005.*
Robust electrocardiogram (ECG) beat classification using discrete wavelet transform, by Minhas et al., published Apr. 2008.*
An integrated ECG feature extraction scheme using PCA and wavelet transform, by Martis et al., published Dec. 2009.*
Heart Arrhythmia Detection Using Continuous Wavelet Transform and Principal Component Analysis with Neural Network Classifier, by Ghorbanian et al., Sep. 2010.*
Wikipedia Principal Component Analysis Web Page, Published Jan. 2012.*

(Continued)

*Primary Examiner* — Jeffrey A Gaffin
*Assistant Examiner* — Thomas Fink
(74) *Attorney, Agent, or Firm* — IPro, Inc.; Na Xu (57) ABSTRACT

Described herein is a method of processing a cardiovascular physiological signal, comprising: decomposing the cardiovascular physiological signal into a first plurality of wavelet coefficients using a wavelet transform; selecting a second plurality of wavelet coefficients from the first plurality of wavelet coefficients, the second plurality being a subset of the first plurality; classifying or clustering the cardiovascular physiological signal into one of a plurality of predetermined classes based on the second plurality of wavelet coefficients using an artificial neural network.

20 Claims, 7 Drawing Sheets

(56) References Cited

OTHER PUBLICATIONS

Classification of ECG Arrhythmias using Multi-Resolution Analysis and Neural Networks, by Prasad et al., published Oct. 2003.*

Heart Arrhythmia Detection Using Continuous Wavelet Transform and Principal Component Analysis with Neural Network Classifier, by Ghorbanian et al. published Sep. 2010.*

A Comparison of the Use of Different Wavelet Coefficients for the Classification of the Electrocardiogram, by Chazal, published Oct. 2000.*

Wavelet Principal Component Analysis and Its Application to Hyperspectral Images; Maya R. Gupta, Nathaniel P. Jacobson; This paper appears in: Image Processing, 2006 IEEE International Conference Issue Date: Oct. 8-11, 2006; On pp. 1585-1588; Location: Atlanta, GA; SSN: 1522-4880.

* cited by examiner

WAVELET MODELING PARADIGMS FOR CARDIOVASCULAR PHYSIOLOGICAL SIGNAL INTERPRETATION

BACKGROUND

Patients with high risks of heart attack can benefit from continuous monitoring of their cardiovascular physiological signals and prompt detection of any early symptom of a heart attack. Such monitoring and detection often require automatic recordation and interpretation of cardiovascular physiological signals in a non-hospital environment such as private homes. However, automatic interpretation of cardiovascular physiological signals is challenging due to factors such as intrinsic physiological signal variability (e.g. pathophysiological artifacts), instrumental inaccuracy and/or inconsistency in operating recording instruments. Any such factor can substantially alter and/or distort the cardiovascular physiological signals, for example morphology and rhythm thereof. There has not been a generally accepted solution to discriminate and/or eliminate the effect of the abovementioned factors.

SUMMARY

Described herein are adaptive and robust methods of processing cardiovascular physiological signals. Cardiovascular physiological signals, as used herein, include signals obtained by electrocardiography, sphygmograph, and/or phonocardiogram.

According to an embodiment, a method referred to as principal wavelet modeling (PWM) comprises decomposing cardiovascular physiological signals into wavelet components using a wavelet transform and selecting certain wavelet components using principal component analysis (PCA). The PWM method can further comprise clustering the selected wavelet components using an artificial neural network. Clustering as used herein means assignment of a set of observations into subsets (called clusters) so that observations in the same cluster are similar in some sense. Clustering is a method of unsupervised learning. The cardiovascular physiological signals can be digitally sampled or digitized into a discrete sequence (i.e. a sequence of data points) before the decomposition. The wavelet transform can be a discrete wavelet transform (DWT) or a continuous wavelet transform (CWT). A DWT is preferred due to a high computational efficiency thereof. A result of a wavelet transform includes a plurality of wavelet coefficients. A number of the wavelet coefficients (also known as "dimension"), which depends on a length of the cardiovascular physiological signals and/or parameters of the wavelet transform, is usually too large to be processed directly by an artificial neural network. PCA can reduce the number of the wavelet coefficients by selecting only those characteristic to the cardiovascular physiological signals.

According to an embodiment, a method referred to as discriminant wavelet modeling (DWM) comprises decomposing the cardiovascular physiological signals into wavelet components using a wavelet transform and selecting certain wavelet components using linear discriminant analysis (LDA). The DWM method can further comprise classifying the selected wavelet components using an artificial neural network. The cardiovascular physiological signals can be digitally sampled or digitized into a discrete sequence before the decomposition. Classification is a method of supervised learning. The wavelet transform can be a discrete wavelet transform (DWT) or a continuous wavelet transform (CWT). A DWT is preferred due to a high computational efficiency thereof. Similar to the prior mentioned PWM method, a result of a wavelet transform includes a plurality of wavelet coefficients and a number thereof is usually too large to be processed directly by an artificial neural network. LDA can reduce the number of the wavelet coefficients by selecting only those characteristic to the cardiovascular physiological signals.

The PWM and DWM methods can attack the variability of signals and interpret them effectively. The PWM and DWM methods integrate wavelet transform and artificial neural networks while maintaining encapsulation of wavelet transform and artificial neural networks in separate modules. It is therefore possible to adjust and/or optimize the wavelet transform and artificial neural networks independently. The PWM and DWM methods reduce the complexity of results of the wavelet transform by evaluating the significance of each result and only supply essential features (principal components) thereof to the artificial neural networks. The PWM and DWM methods thus reduce the overall computational cost in processing the cardiovascular physiological signals and provide adaptive and robust interpretation and classification of the cardiovascular physiological signals.

According to an embodiment, a method of processing a cardiovascular physiological signal, comprises: decomposing the cardiovascular physiological signal into a first plurality of wavelet coefficients using a wavelet transform; selecting a second plurality of wavelet coefficients from the first plurality of wavelet coefficients, the second plurality being a subset of the first plurality; classifying or clustering the cardiovascular physiological signal into one of a plurality of predetermined classes based on the second plurality of wavelet coefficients using an artificial neural network.

DETAILED DESCRIPTION

Processing complex systems such as cardiovascular physiological signals can benefit from an approach combining soft computing and hard computing. Hard computing (HC) attempts to model a system exactly. HC techniques are largely based on formal logical systems, such as sentential logic and predicate logic, or rely heavily on computer-aided numerical analysis (such as finite element analysis). However, HC is not always possible or practicable in relatively complex systems, such as those of practical interest in biology, medicine, humanities, management sciences, etc. Such complex systems can be intrinsically chaotic, have too many variables, and/or have poorly understood underlying mechanisms. Soft computing (SC), unlike HC, allows imprecision, uncertainty, partial truth, and approximation to achieve tractability, robustness and low solution cost. Exemplary SC techniques include neural networks, fuzzy systems, evolutionary computation (e.g. evolutionary algorithms, harmony search), swarm intelligence, ideas about probability (e.g. Bayesian network), chaos theory, perceptron, etc. Generally speaking, SC techniques tend to provide adaptiveness and HC techniques tend to provide robustness. SC and HC can be complement in certain systems, such as in processing of cardiovascular physiological signals as described herein.

According to embodiments herein, artificial neural networks are used as an exemplary SC technique for adaptive clustering or classification of cardiovascular physiological signals; wavelet transforms are used as an exemplary HC technique for robust identification of features in cardiovascular physiological signals.

An artificial neural network (ANN), also referred to as "neural network" (NN), is a mathematical model or computational method that is inspired by the structure and/or functional aspects of biological neural networks. An artificial neural network consists of an interconnected group of artificial neurons, and processes information using a connectionist approach to computation. In many cases an ANN is an adaptive system that can change its structure based on external or internal information that flows through the ANN during a learning phase. An ANN can be a non-linear statistical data modeling tool and can be used to model complex relationships between inputs and outputs or to find patterns in data. An artificial neuron is a mathematical function conceived as a crude model, or abstraction of biological neurons. Artificial neurons are the constitutive units in an ANN. Depending on specific forms, an artificial neuron can receive different names, such as semi-linear unit, Nv neuron, binary neuron, linear threshold function or McCulloch-Pitts neuron. An artificial neuron receives one or more inputs (corresponding to the one or more dendrites of a biological neuron) and calculates an output (corresponding to the synapse of a biological neuron) from the one or more inputs. A connectionist approach is an approach in the fields of artificial intelligence, cognitive psychology, cognitive science, neuroscience and philosophy of mind that models mental or behavioral phenomena as the emergent processes of interconnected networks of simple units. According to an embodiment, an ANN is used to discover relationships of features in cardiovascular physiological signals identified by a HC technique such as wavelet transform.

Wavelet transform is a method of decomposing a signal in the time domain into the time-frequency representation. A wavelet is a wave-like oscillation with an amplitude that starts out at zero, increases, and then decreases back to zero. In essence, wavelet transform on a signal in the time domain reveals spectral components composing the signal and temporal locations of the spectral components. The term "time domain" should be understood broadly to include any domain on which a signal is defined. In a mathematical form, a continuous wavelet transform (CWT) of a function $f(x)$ can be defined as:

$$CWT_f^\psi(\tau, s) = \frac{1}{\sqrt{|s|}} \int_{-\infty}^{\infty} f(x) \psi^*\left(\frac{x-\tau}{s}\right) dx,$$

wherein $\tau$ and $s$ are the translation and scale parameters, respectively. $\psi$ is called the mother wavelet. $\psi^*$ is the complex conjugate of $\psi$. Exemplary mother wavelets include the Meyer wavelet, Morlet wavelet, and the Mexican hat wavelet. As stated above, the variable x is not limited to time but can be any variable.

A discrete wavelet transform (DWT) is any wavelet transform for which the wavelets are mutually orthogonal set of discrete wavelets sampled from a CWT. The discrete wavelets can be sampled from a CWT on a grid $(s, \tau)$, wherein $s=s_0^j$ and $\tau=k\tau_0 s_0^j$, as $$\psi_{j,k}(t) = \frac{1}{\sqrt{s_0^j}} \psi\left(\frac{t - k\tau_0 s_0^j}{s_0^j}\right).$$

Although the discrete wavelets are referred to as "discrete", they are (piecewise or stepwise) continuous functions. j and k are integers and $s_0 > 1$ is a constant called the dilation step. $\tau_0$ is a constant called the translation factor. When $s_0=2$ and $\tau_0=1$, the grid $(s, \tau)$ is known as the dyadic grid.

Figure 2:
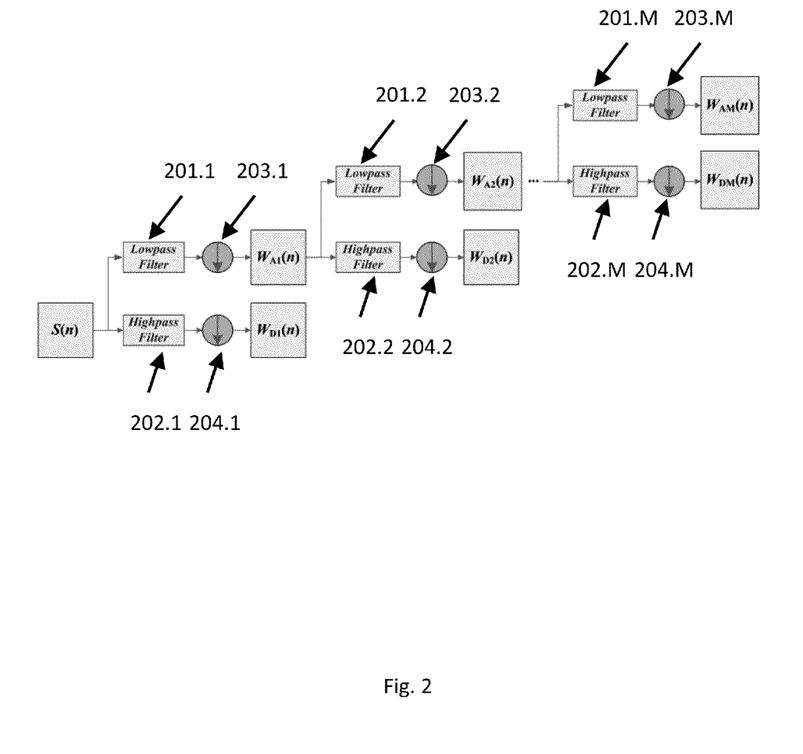
FIGS. 2 and 3 are illustrative diagrams of discrete wavelet transform.
Figure 3:
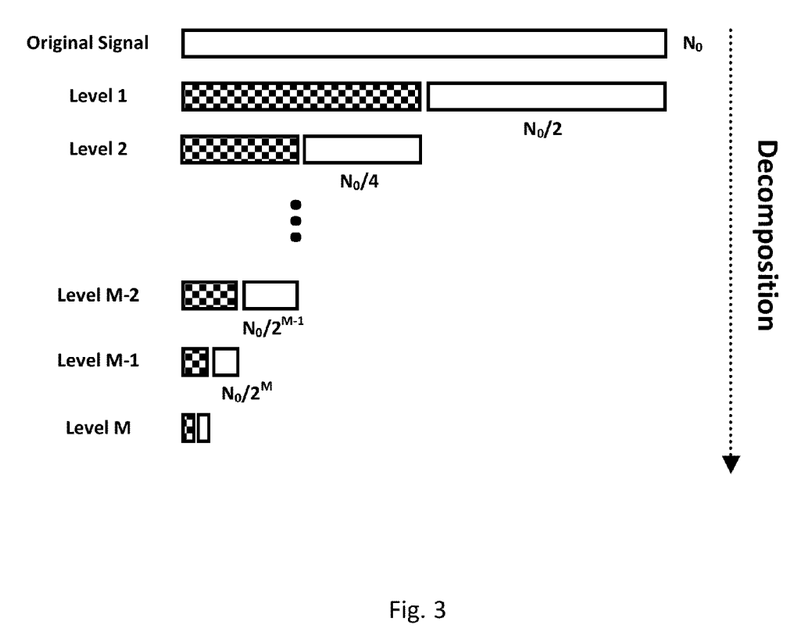

An exemplary algorithm implementing a DWT is illustrated in more details in FIGS. 2 and 3. A signal is digitized into a discrete sequence $s(n)$ ($n=1, 2, \ldots, N_0$) wherein $N_0$ is the length of sequence, i.e. discrete sequence $s(n)$ has $N_0$ data points. As shown in FIG. 2, $s(n)$ is convoluted with a lowpass filter function 201.1 and downsampled in a downsample step 203.1 into an approximation sequence $W_{A1}(n)$; $s(n)$ is also convoluted with a highpass filter function 202.1 and downsampled in a downsample step 204.1 into a plurality of wavelet coefficients $W_{D1}(n)$. The approximation sequence $W_{A1}(n)$ is convoluted with a lowpass filter function 201.2 and downsampled in a downsample step 203.2 into an approximation sequence $W_{A2}(n)$; $W_{A1}(n)$ is also convoluted with a highpass filter function 202.2 and downsampled in a downsample step 204.2 into a plurality of wavelet coefficients $W_{D2}(n)$. These steps are repeated M times until an approximation sequence $W_{AM}(n)$ has only one point. All the wavelet coefficients $W_{Dm}(n)$, wherein $m=1, 2, \ldots M$, can be concatenated into a vector.

The lowpass filters 201.$m$ and the highpass filters 202.$m$, wherein $m=1, 2, \ldots M$, are also referred as scale filters $h(n)$ and wavelet filters $g(n)$, respectively. The convolution of $s(n)$ with the lowpass filters 201.$m$ and the highpass filters 202.$m$, wherein $m=1, 2, \ldots M$, is defined as $$s(n) * h(n) = \sum_{k=-\infty}^{\infty} s(k) \cdot h(n-k) \text{ and } s(n) * g(n) = \sum_{k=-\infty}^{\infty} s(k) \cdot g(n-k).$$

The downsample steps 204.$m$, wherein $m=1, 2, \ldots M$, simply discard every other date point. So the derivation of $W_{A1}(n)$ can mathematically be expressed as $$W_{A1}(n) = \sum_{k=-\infty}^{\infty} h(k) \cdot s(2n-k)$$

while $W_{D1}(n)$ can mathematically be expressed as $$W_{D1}(n) = \sum_{k=-\infty}^{\infty} g(k) \cdot s(2n-k); \text{ and } W_{Am}(n) = \sum_{k=-\infty}^{\infty} h(k) \cdot W_{A(m-1)}(2n-k),$$

$$W_{Dm}(n) = \sum_{k=-\infty}^{\infty} g(k) \cdot W_{D(m-1)}(2n-k),$$

wherein m=2, 3, ..., M. The filters h(n) and g(n) satisfy the criterion of Quadrature Mirror Filters (QMF): $g(L-1-n)=(-1)^n \cdot h(n)$ where L is the filter length (in number of points).

Wavelet transform is a well-established technology for unified time-frequency analysis. However, wavelet transform on cardiovascular physiological signals produces a large number of wavelet components, wherein many of the wavelet components correspond to noises and artifacts and only a small fraction of the wavelet components represent essential features (i.e. features useful for classification and/or interpretation) of the cardiovascular physiological signals. Discarding those wavelet components corresponding to noises and artifacts and selecting only those wavelet components representing the essential features can greatly enhance accuracy of classification and/or interpretation of the cardiovascular physiological signals and thus lead to accurate and prompt detection of abnormal heart conditions. One approach to select the wavelet components representing the essential features is so-called "energy maximization", wherein wavelet components whose wavelet coefficients are above a predetermined threshold are selected. This technique attempts to select out strong wavelet components. Exemplary techniques that fall under the scope of energy maximization include wavelet scale maxima, relative wavelet energies and regional wavelet entropies. Another approach is directed to select those wavelet components that morphologically approximate the cardiovascular physiological signals. Exemplary techniques that fall under the scope of morphological approximation include wavelet shrinkage, matching pursuits and wavelet regression networks.

However, neither of these two approaches guarantees that the selected wavelet components are suitable for accurate classification of the cardiovascular physiological signals. Some of wavelet components are coincident in a time-frequency representation, i.e. those wavelet components selected for having large wavelet coefficients are often selected for morphological approximation. For classification of the cardiovascular physiological signals, identifying similarities of cardiovascular physiological signals belonging to a same class (e.g. normal cardiovascular physiological signals, or cardiovascular physiological signals from patients with a specific heart condition such as arrhythmia) and differences of cardiovascular physiological signals belonging to different classes is of particular importance, which neither the approach of energy maximization nor the approach of morphological approximation takes into account.

Figure 1:
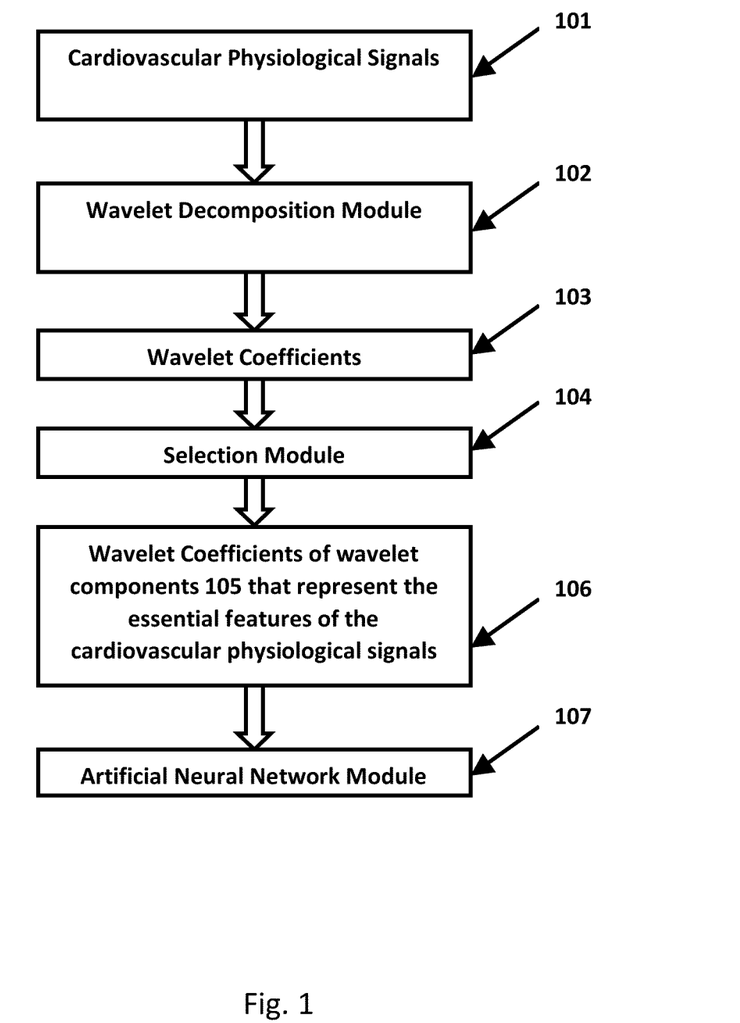
FIG. 1 shows a flowchart of a method according to an embodiment.

FIG. 1 shows a general flowchart of a method of processing cardiovascular physiological signals according to an embodiment. A plurality of cardiovascular physiological signals 101 is provided. A wavelet decomposition module 102 decomposes each of the cardiovascular physiological signals 101 using a wavelet transform into a plurality of wavelet coefficients 103. Each of the wavelet coefficients 103 corresponds to a wavelet component of the wavelet transform. The cardiovascular physiological signals 101 are preferably digitally sampled or digitized into a discrete sequence. The wavelet transform is preferably a DWT.

A selection module 104 selects wavelet coefficients 106 of those wavelet components 105 that preferably represent the essential features of the cardiovascular physiological signals 101. The wavelet coefficients 106 are input into an artificial neural network module 107. The artificial neural network module 107 classifies the cardiovascular physiological signals 101 into one of a plurality of predetermined classes (e.g. normal cardiovascular physiological signals, abnormal cardiovascular physiological signals indicating a particular abnormal heart condition) based on the wavelet coefficients 106 of each of the cardiovascular physiological signals 101. The wavelet coefficients 106 are a subset of the wavelet coefficients 103.

The artificial neural network module 107 can be any suitable artificial neural network such as a self-organizing map (SOM), which is also called as a self-organizing feature map (SOFM). According to an embodiment, the artificial neural network module 107 comprises a SOM. A SOM is a type of artificial neural network that is trained using unsupervised learning to produce a low-dimensional (typically two-dimensional), discretized representation of the input space of the training samples, called a map. Self-organizing maps are different from other artificial neural networks in the sense that they use a neighborhood function to preserve the topological properties of the input space. A SOM is useful for visualizing low-dimensional views of high-dimensional data, akin to multidimensional scaling. Like most artificial neural networks, SOMs operate in two modes: training and mapping. In the training mode, a set of signals (training samples) with known classification are input into a SOM and the SOM adapts to the training samples. In the mapping mode, the SOM classifies unclassified signals.

Figure 4:
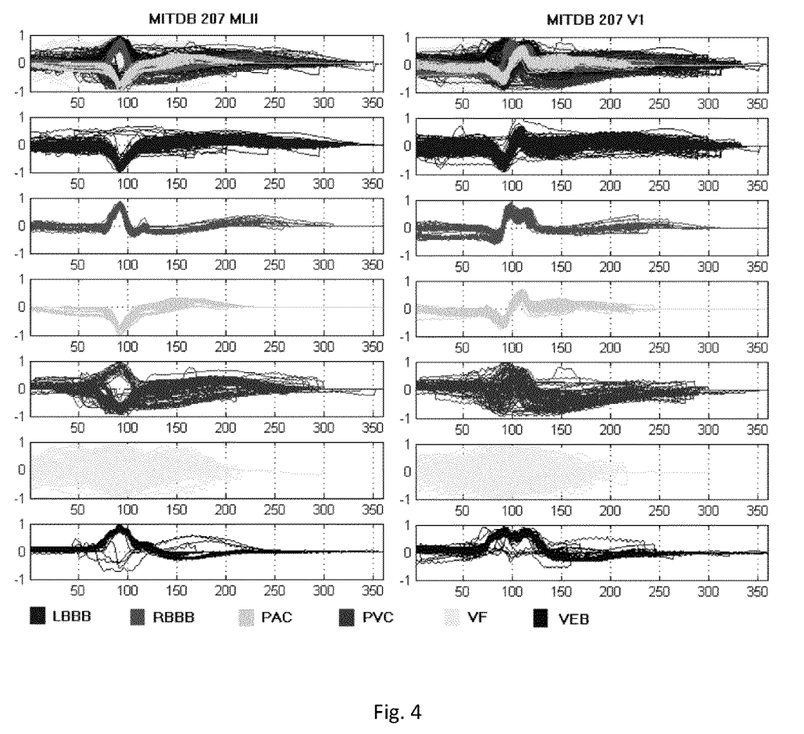
FIG. 4 shows exemplary cardiovascular physiological signals obtained by electrocardiography (ECG) from patients with arrhythmia (also known as "cardiac dysrhythmia"), wherein these particular exemplary cardiovascular physiological signals are retrieved from a benchmark database: MIT/BIH Arrhythmia Database (MAD).

FIG. 4 shows exemplary cardiovascular physiological signals that can be processed by the method shown in FIG. 1. The signals in FIG. 4 are retrieved from the recording 207 of the MIT/BIH Arrhythmia Database (MAD) workbench. It consists of 2 leads of synchronous ECG recordings, namely MLII and V1. There are 6 types of arrhythmia patterns indentified by medical experts. The different morphological types of arrhythmia ECGs often intertwine together, as the first graph of each column in FIG. 4 shows. At the same time, the single group of arrhythmia ECGs often has diversified morphologies, which are marked with different shades as shown in FIG. 4.

According to an embodiment, the selection module 104 selects the wavelet coefficients 106 using PCA.

PCA is a method that selects essential features from a set of data, each of the data consists of a set of values of a number of possibly correlated variables. PCA includes using an orthogonal transformation to map the possibly correlated variables to a number of uncorrelated (i.e. orthogonal) variables such that a first uncorrelated variable has the highest possible variance in the set of data, a second uncorrelated variable has the second highest possible variance in the set of data, ..., a m-th uncorrelated variable has the m-th highest possible variance in the set of data. The number of the uncorrelated variables is smaller than the number of the correlated variables. Variance of a variable X can be defined as $\sigma_X^2 = E[X^2] - (E[X])^2$. Any two of the uncorrelated variables are uncorrelated, i.e. a correlation coefficient between the two uncorrelated variables is zero. The correlation coefficient $\rho_{X,Y}$ between two variables X and Y with expected values $\mu_X$ and $\mu_Y$ and standard deviations $\sigma_X$ and $\sigma_Y$, respectively, can be defined as:

$$\rho_{X,Y} = \frac{E[(X-\mu_X)(Y-\mu_Y)]}{\sigma_X \sigma_Y},$$

where E is the expected value operator, $\mu_X$ and $\mu_Y$ are the expected values of X and Y, $\sigma_X$ and $\sigma_Y$ are the standard deviations of X and Y. The uncorrelated variables are referred to as principal components. PCA can be thought of as revealing the internal structure of the data in a way which best explains the variance in the data. If a set of data with a large number of variables, PCA can provide the most "informative" viewpoint of the set of data, by selecting only the first few principal components, which represent essential features of the set of data.

Figure 5:
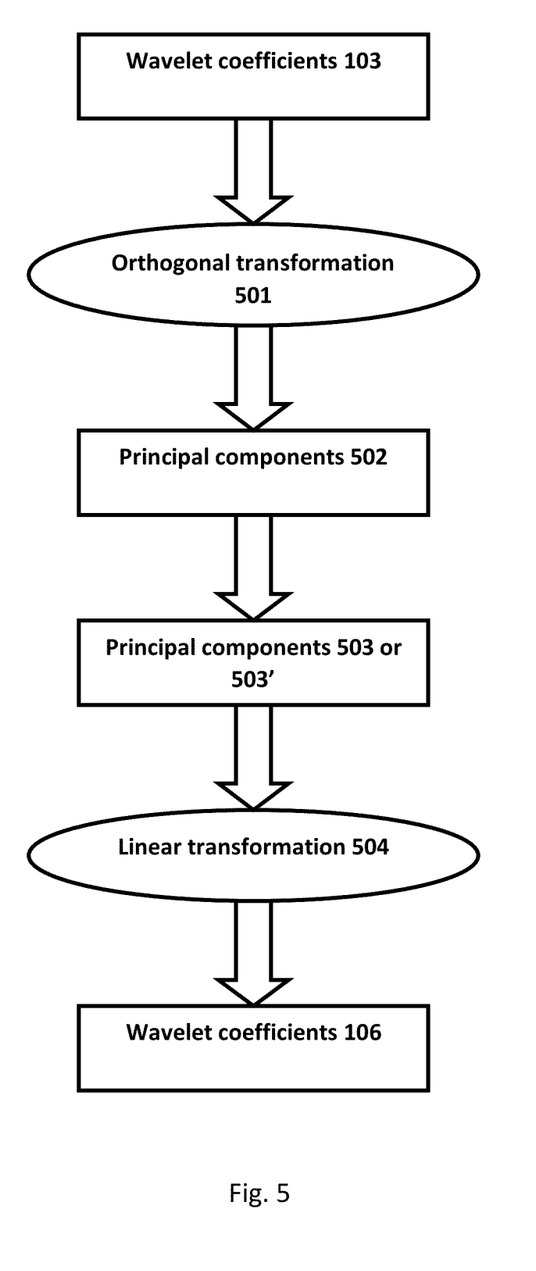
FIG. 5 shows a flowchart for selecting wavelet coefficients according to an embodiment.

Specifically, according to an embodiment and as shown in FIG. 5, the selection module 104 uses an orthogonal transformation 501 to map the wavelet coefficients 103 into a plurality of principal components 502. A variance of each of the principal components 502 is computed. Only those principal components 503 having variances greater than a predetermined threshold value are selected. Alternatively, only a predetermined number of the principal components 503' are selected that have the greatest variances among all the principal components 502 (i.e. the variance of any of the principal components 503' is not smaller than the variance of any principal component 502 that is not one of the principal components 503'). The wavelet coefficients 106 are derived by transforming the selected principal components 503 or 503' by a linear transformation 504 that is a reverse transformation of the orthogonal transformation 501.

Figure 6:
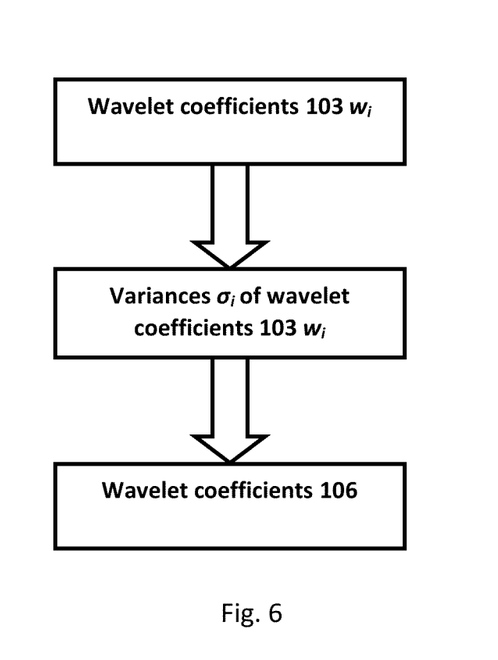
FIG. 6 shows a flowchart for selecting wavelet coefficients according to an embodiment.

According to an embodiment and as shown in FIG. 6, the selection module 104 selects the wavelet coefficients 106 based on variances of the wavelet coefficients 103. A variance of each of the wavelet coefficients 103 is calculated. Only those wavelet coefficients 103 having variances greater than a predetermined threshold value are selected as the wavelet coefficients 106. Alternatively, only a predetermined number of the wavelet coefficients 103 having the greatest variances among all the wavelet coefficients 103 are selected as the wavelet coefficients 106.

Figure 7:
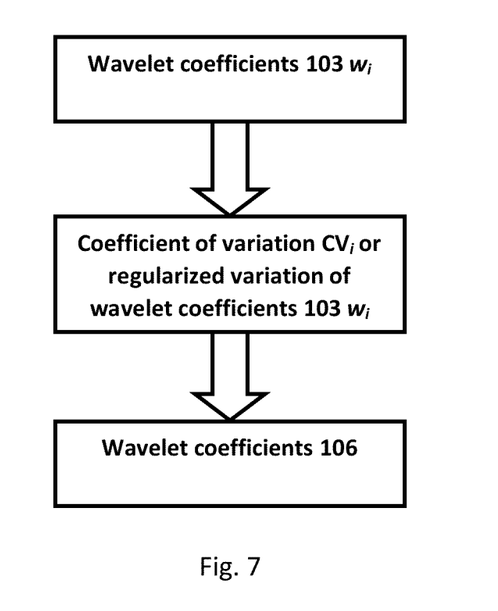
FIG. 7 shows a flowchart for selecting wavelet coefficients according to an embodiment.

According to an embodiment and as shown in FIG. 7, the selection module 104 selects the wavelet coefficients 106 based on regularized variances or coefficients of variation of the wavelet coefficients 103. A coefficient of variation or a regularized variance of each of the wavelet coefficients 103 is computed. Only those wavelet coefficients 103 having coefficients of variation or regularized variance greater than a predetermined threshold value are selected as the wavelet coefficients 106. Alternatively, only a predetermined number of the wavelet coefficients 103 having the greatest coefficients of variation or the greatest regularized variances among all the wavelet coefficients 103 are selected as the wavelet coefficients 106. A coefficient of variation (CV) of a variable X, also known as unitized risk or the variation coefficient, is defined as the ratio of the standard deviation $\sigma_X$ of the variable X to the expected value $\mu_X$ of the variable X. A regularized variance of a variable X, as used herein, is defined as the ratio of the variance $\sigma_X^2$ of the variable X to the expected value $\mu_X$ of the variable X.

Figure 8:
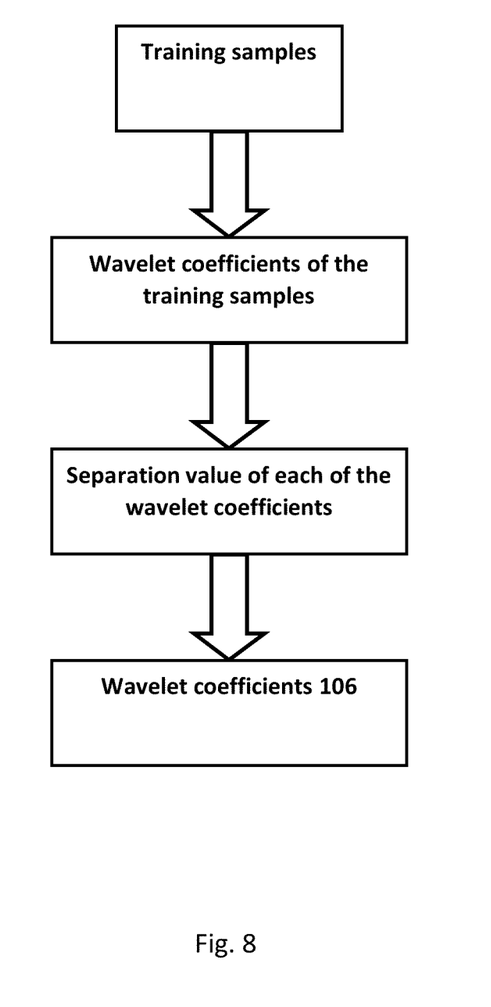
FIG. 8 shows a flowchart for selecting wavelet coefficients according to an embodiment.

According to an embodiment and as shown in FIG. 8, the selection module 104 selects the wavelet coefficients 106 based on separation values of each wavelet coefficients 103 computed from a set of cardiovascular physiological signals (i.e. training samples, or a training set) wherein each of the cardiovascular physiological signals is known to belong to one of the predetermined classes and at least one of cardiovascular physiological signals belongs to each given one of the predetermined classes. For clarity, the set of cardiovascular physiological signals are denoted as $s_{i,j}$, wherein i=1, 2, ..., $n_j$, j=1, 2, ..., C, C is the number of the predetermined classes; $n_j$ is the number of the cardiovascular physiological signals in the set that belong to the j-th class of the predetermined classes. Each cardiovascular physiological signal $s_{i,j}$ can be decomposed by the wavelet decomposition module 102 into wavelet coefficients $w_{i,j,l}$, wherein l=1, 2, ..., L, L is the total number of the wavelet coefficients $w_{i,j,l}$. For the l-th wavelet coefficient, a separation value $S_l$ can be computed as $$S_l = \frac{\sum_{j=1}^{C} n_j (\mu_{l,j} - M_l)^2}{\sum_{j=1}^{C} \sum_{i=1}^{n_j} (w_{i,j,l} - \mu_{l,j})^2},$$

wherein $\mu_{l,j}$ is an expected value of the l-th wavelet coefficient within the j-th class $$\left( \mu_{l,j} = \frac{1}{n_j} \sum_{i=1}^{n_j} w_{i,j,l} \right),$$

$M_l$ is an expected value of the l-th wavelet coefficient within the entire set across all classes $$\left( M_l = \left( \sum_{j=1}^{C} \sum_{i=1}^{n_j} w_{i,j,l} \right) \Big/ \sum_{j=1}^{C} n_j \right).$$

Only those wavelet coefficients $w_{i,j,l}$ having a separation value $S_l$ greater than a predetermined threshold value are selected as the wavelet coefficients 106. Alternatively, only a predetermined number of the wavelet coefficients $w_{i,j,l}$ having the greatest separation values $S_l$ among all the wavelet coefficients $w_{i,j,l}$ are selected as the wavelet coefficients 106. A large $S_l$ value indicates the l-th wavelet coefficient has a small variance within each class and/or expected value of the l-th wavelet coefficient within any class has a large variance across all the classes, i.e. the l-th wavelet coefficient is a good indicator of the classes. The selected wavelet coefficients 106 can be input into a suitable neural network 107 such as a probabilistic neural network (PNN).

An exemplary PNN algorithm is shown in the program listing below:

```
//C is the number of classes, N is the number of examples, Nk are from
class k, d is the dimensionality of the training examples, sigma is the
smoothing factor, test_example[d] is the example to be classified and
Examples[N][d] are the training examples
int PNN (int C, int N, int d, float sigma, float test_example[d], float
Examples[N][d]) {
    int classify = -1;
    float largest = 0;
    float sum[ C ];
    // The Output Layer which computes the pdf for each class C
    for ( int k=1; k<=C; k++ ) {
        sum[ k ] = 0;
        // The Summation Layer which accumulates the probabilistic
        density function
        // for each example from the particular class k
        for ( int i=0; i<Nk; i++ ) {
            float product = 0;
            // The Pattern Layer that multiplies the test example by
            the weights
            for ( int j=0; j<d; j++ )
                product += test_example[j] * Examples[i][j];
```

-continued

```
        product = ( product - 1 ) / ( sigma * sigma );
        product = exp( product );
        sum[ k ] += product;
        }
      sum[ k ] /= Nk;
      }
   for ( int k=1; k<=C; k++ )
      if ( sum[ k ] > largest ) {
         largest = sum[ k ];
         classify = k;
         }
   return classify;
}
```

It will be appreciated that the methods described above may be practiced by hand or otherwise suitable, for example, by a computer executing a computer program containing one or more sequences of machine-readable instructions describing a method as disclosed above. The methods described above can also be in a form of a non-transitory data storage medium (e.g. semiconductor memory, magnetic or optical disk) having such a computer program stored therein.

In relation to the claims, it is intended that when words such as "a," "an," "at least one," or "at least one portion" are used to preface a feature there is no intention to limit the claim to only one such feature unless specifically stated to the contrary in the claim.

The descriptions above are intended to be illustrative, not limiting. Thus, it will be apparent to one skilled in the art that modifications may be made without departing from the scope of the claims set out below.

We claim:

1. A method of processing a cardiovascular physiological signal, comprising:
    decomposing the cardiovascular physiological signal into a first plurality of wavelet coefficients using a wavelet transform;
    selecting a second plurality of wavelet coefficients from the first plurality of wavelet coefficients, the second plurality being a subset of the first plurality;
    classifying or clustering the cardiovascular physiological signal into one of a plurality of predetermined classes based on the second plurality of wavelet coefficients using an artificial neural network; and
    computing a regularized variance of each of the first plurality of wavelet coefficients, wherein the second plurality of wavelet coefficients are selected based on the regularized variance.

2. The method of claim 1, wherein the cardiovascular physiological signal is a signal obtained by electrocardiography, sphygmograph, and/or phonocardiogram.

3. The method of claim 1, further comprising digitally sampling or digitizing the cardiovascular physiological signal into a discrete sequence.

4. The method of claim 1, wherein the artificial neural network is a self-organizing map or a probabilistic neural network.

5. The method of claim 1, wherein the wavelet transform is a continuous wavelet transform.

6. The method of claim 1, wherein the wavelet transform is a discrete wavelet transform.

7. The method of claim 1, wherein the wavelet transform uses a mother wavelet selected from the group consisting of Meyer wavelet, Morlet wavelet and Mexican hat wavelet.

8. The method of claim 1, wherein the second plurality of wavelet coefficients include all of the first plurality of wavelet coefficients that have regularized variance greater than a predetermined threshold value.

9. The method of claim 1 wherein the second plurality of wavelet coefficients include a predetermined number of wavelet coefficients of the first plurality of wavelet coefficients that have the greatest regularized variance among all the wavelet coefficients of the first plurality of wavelet coefficients.

10. A method of processing a cardiovascular physiological signal, comprising:
    decomposing the cardiovascular physiological signal into a first plurality of wavelet coefficients using a wavelet transform;
    selecting a second plurality of wavelet coefficients from the first plurality of wavelet coefficients, the second plurality being a subset of the first plurality;
    classifying or clustering the cardiovascular physiological signal into one of a plurality of predetermined classes based on the second plurality of wavelet coefficients using an artificial neural network; and
    computing separation values of the first plurality of wavelet coefficients using a training set of cardiovascular physiological signals, wherein the second plurality of wavelet coefficients are selected based on the separation values of the first plurality of wavelet coefficients, wherein each of the cardiovascular physiological signals of the training set is known to belong to one of the predetermined classes and at least one of cardiovascular physiological signals of the training set belongs to each given one of the predetermined classes.

11. The method of claim 10, wherein the second plurality of wavelet coefficients include all of the first plurality of wavelet coefficients that have separation values greater than a predetermined threshold value.

12. The method of claim 10, the second plurality of wavelet coefficients include a predetermined number of wavelet coefficients of the first plurality of wavelet coefficients that have the greatest separation values among all the wavelet coefficients of the first plurality of wavelet coefficients.

13. A computer program product comprising a non-transitory computer readable medium having instructions recorded thereon, then instructions when executed by a computer implementing the method of claim 1.

14. A method of processing a cardiovascular physiological signal, comprising:
    decomposing the cardiovascular physiological signal into a first plurality of wavelet coefficients using a wavelet transform;
    selecting a second plurality of wavelet coefficients from the first plurality of wavelet coefficients, the second plurality being a subset of the first plurality;
    classifying or clustering the cardiovascular physiological signal into one of a plurality of predetermined classes based on the second plurality of wavelet coefficients using an artificial neural network; and
    computing a coefficient of variation of each of the first plurality of wavelet coefficients, wherein the second plurality of wavelet coefficients are selected based on the coefficients of variation.

15. The method of claim 14, wherein the second plurality of wavelet coefficients include all of the first plurality of wavelet coefficients that have coefficients of variation greater than a predetermined threshold value.

16. The method of claim 14, the second plurality of wavelet coefficients include a predetermined number of wavelet coefficients of the first plurality of wavelet coefficients that have the greatest coefficients of variation among all the wavelet coefficients of the first plurality of wavelet coefficients.

17. A computer program product comprising a non-transitory computer readable medium having instructions recorded thereon, then instructions when executed by a computer implementing the method of claim 10.

18. A computer program product comprising a non-transitory computer readable medium having instructions recorded thereon, then instructions when executed by a computer implementing the method of claim 14.

19. The method of claim 10, wherein the cardiovascular physiological signal is a signal obtained by electrocardiography, sphygmograph, and/or phonocardiogram.

20. The method of claim 14, wherein the cardiovascular physiological signal is a signal obtained by electrocardiography, sphygmograph, and/or phonocardiogram.

* * * * *